United States Patent

Sredniawski

[11] Patent Number: 5,784,430
[45] Date of Patent: Jul. 21, 1998

[54] MULTIPLE STATION GAMMA RAY ABSORPTION CONTRABAND DETECTION SYSTEM

[75] Inventor: Joseph J. Sredniawski, Northport, N.Y.

[73] Assignee: Northrop Grumman Corporation, Los Angeles, Calif.

[21] Appl. No.: 632,954

[22] Filed: Apr. 16, 1996

[51] Int. Cl.$^6$ .................................................. G01N 23/04
[52] U.S. Cl. ............................ 378/57; 378/143; 378/144
[58] Field of Search .............................. 378/57, 144, 143

[56] References Cited

U.S. PATENT DOCUMENTS

| | | | |
|---|---|---|---|
| 3,609,432 | 9/1971 | Shimula | 313/59 |
| 4,163,901 | 8/1979 | Azam et al. | 250/401 |
| 4,323,780 | 4/1982 | Tombaugh et al. | 250/419 |
| 4,618,972 | 10/1986 | Georgian et al. | 378/34 |
| 4,637,042 | 1/1987 | Braun | 378/143 |
| 4,674,109 | 6/1987 | Ono | 378/130 |
| 4,768,212 | 8/1988 | Appelt et al. | 378/141 |
| 4,945,562 | 7/1990 | Staub | 378/130 |
| 5,040,200 | 8/1991 | Ettinger et al. | 378/88 |
| 5,068,883 | 11/1991 | DeHaan et al. | 378/86 |
| 5,098,640 | 3/1992 | Gozani et al. | 376/166 |
| 5,115,459 | 5/1992 | Bertozzi | 378/88 |
| 5,159,617 | 10/1992 | King et al. | 378/57 |
| 5,199,054 | 3/1993 | Adams et al. | 378/21 |
| 5,227,800 | 7/1993 | Huguenin et al. | 342/179 |
| 5,251,240 | 10/1993 | Grodzins | 376/157 |
| 5,282,235 | 1/1994 | Schmor et al. | 378/53 |

*Primary Examiner*—Craig E. Church
*Attorney, Agent, or Firm*—Terry J. Anderson; Karl J. Hoch, Jr.

[57] ABSTRACT

A multiple station gamma ray absorption contraband detection system utilizes a proton source and disk-shaped target to provide a 360 degree resonant gamma ray cone which is suitable for use in four separate gamma ray absorption contraband detection stations simultaneously. The target has two beryllium walls coated with $^{13}C$ and $^{34}S$ so as to facilitate the detection of nitrogen and chlorine in a manner which reliably and effectively identifies contraband such as explosives and drugs via gamma ray absorption.

15 Claims, 7 Drawing Sheets

MULTIPLE STATION GAMMA RAY ABSORPTION CONTRABAND DETECTION SYSTEM

FIELD OF THE INVENTION

The present invention relates generally to the detection of contraband, e.g., drugs and explosives, via the selective absorption of gamma rays. It relates more particularly to an improved target which facilitates the construction of multiple contraband detection stations utilizing a common proton source for the generation of gamma rays.

BACKGROUND OF THE INVENTION

The need to detect contraband such as drugs and explosives is well appreciated. Drugs are routinely smuggled through various ports of entry such as airports, border crossings, and boat docks. Efforts to control the flow of such contraband have increased substantially over the years. Various means, including manual searches, drug sniffing dogs, and X-ray devices are frequently utilized in an attempt to locate such contraband.

The smuggling of explosives, particularly aboard aircraft, has become of great concern recently. This is particularly true in light of recent airline bombings involving great loss of life. Again, various techniques such as manual searching, dogs, and X-rays are routinely used in order to prevent such smuggling.

However, as those skilled in the art will appreciate, such contemporary contraband detection techniques are much less effective than desirable. Manual searching is extremely time consuming and costly. Manual searching is also intrusive, and therefore objectionable to the owners of the searched containers.

The use of dogs to search for drugs and/or explosives requires that a trained and experienced dog and handler be utilized. This is very inefficient and also strictly limits the quantity of baggage that can be so searched.

The use of X-rays has been found to be unreliable, since it is possible to disguise or camouflage drugs and/or explosives in a manner which makes them extremely difficult to detect therewith. Even experienced X-ray machine operators are not capable of detecting such camouflaged contraband in some cases.

In view of the above-mentioned deficiencies in the art, various non-intrusive scanning techniques have been developed which are more accurate than contemporary X-ray techniques. It is known to utilize neutron activation and selective gamma ray absorption to identify elements, typically chlorine, oxygen, and/or nitrogen, which are generally present in such contraband. Examples of devices which utilize gamma rays to detect contraband are provided in U.S. Pat. Nos. 5,040,200 issued on Aug. 13, 1991 to Ettinger et al.; 5,068,883 issued on Nov. 26, 1991 to DeHaan et al.; 5,159,617 issued on Oct. 27, 1992 to King et al.; 5,251,240 issued on Oct. 5, 1993 to Grodzins; and 5,282,235 issued on Jan. 25, 1994 to Schmor et al.

However, although such gamma ray absorption techniques are non-intrusive and generally reliable, they are extremely expensive to practice. A gamma ray absorption contraband detection device which is suitable for use in high-capacity applications, such as airports, boat docks, and border crossings, must utilize a comparatively strong gamma ray source, such as a proton accelerator. Such a device generates gamma rays by focusing a beam of energetic protons upon a target. The incident proton beam excites the material of the target according to well known principles, thereby causing it to produce gamma rays.

In order to prevent rapid deterioration of the target, contemporary systems utilize a drum-shaped target which rotates, so as to limit the exposure of any particular portion of the target to the proton beam, thereby increasing the surface area upon which the proton beam is incident and consequently facilitating cooling thereof. Further, water cooling is typically utilized to facilitate heat dissipation from the target. One example of a watercooled target is provided in U.S. Pat. No. 4,323,780 issued on Apr. 6, 1982 to Tombaugh et al.

However, a problem common to contemporary targets is that they form a 360 degree gamma ray beam which, due to interaction with the target structure (shape), typically approximately 53 degrees of the gamma cone beam is suitable for use. This limits use to only a single contraband detection station. Thus, according to the prior art, each individual contraband detection station requires a separate, dedicated target and proton accelerator. Because of the high cost associated with the construction and maintenance of a proton accelerator suitable for use in such contraband detection, it would be extremely beneficial to provide a single proton accelerator suitable for use in the generation of a gamma ray beam which may be used in multiple contraband detection stations.

SUMMARY OF THE INVENTION

The present invention specifically addresses and alleviates the above-mentioned deficiencies associated with the prior art. More particularly, the present invention comprises a multiple station gamma ray absorption contraband detection system. The contraband detection system comprises a proton source, e.g., a linear proton accelerator, and a target upon which protons from the proton source are incident. The target of the present invention comprises a disk formed of an alloy of beryllium which is configured to be rotatable within the proton beam. The disk provides a 360 resonant gamma ray cone so as to facilitate the operation of plural detection stations simultaneously therewith.

According to a preferred embodiment of the present invention, the plural contraband detection stations each utilize between approximately 45 degrees and approximately 90 degrees, preferably approximately 53 degrees, of the gamma ray beam. As those skilled in the art will appreciate, four contraband detection stations can readily be accommodated when each station utilizes approximately 53 degrees of the 360 degrees resonant gamma ray cone.

A conveyor is preferably utilized to transport a test article, i.e., baggage, into that portion of the gamma ray cone used by a particular station. At least one detector is configured to sense gamma rays which have passed through the test article. The conveyor is preferably configured so as to translate and rotate the test article within the proton beam, such that the proton beam passed through substantially all portions of the test article.

A plurality of gamma ray detectors, preferably two horizontal rows of detectors generally defining an arc, are preferably utilized, so as to more efficiently scan the test article, thereby increasing performance. The use of such a plurality of gamma ray detectors further facilitates tomographic imaging, so as to further enhance reliability.

According to the preferred embodiment of the present invention, the system also comprises a plurality of containers, preferably drums, into which the individual test articles are placed, so as to facilitate their being moved into the gamma ray cone at each detection station. Thus, a plurality of suitcases, preferably approximately 18, are placed into a drum and processed together, so as to increase the throughput of the system.

A conveyor system preferably comprises at least one incoming conveyor belt for bringing each container to a position near the translation and rotation tables, and a first handler for each incoming conveyor belt for moving the container from the incoming conveyor belt to a selected one of the rotation and translation tables. At least one outgoing conveyor belt receives the scanned containers from the rotation and translation tables, via a second handler. Those skilled in the art will appreciate that various mechanical handling devices are suitable for transferring drums between a conveyor belt and a table.

According to the preferred embodiment of the present invention, four tables disposed approximately 90 degrees apart from one another about a common center rotate and translate each container during the scanning process. Two incoming conveyor belts, disposed approximately 180 degrees apart from one another about the common center each bring the containers near two of the tables. The first handler associated with each of the incoming conveyor belts then moves an incoming container from the conveyor belt to a selected one of the two nearby tables. Four outgoing conveyor belts are preferably then utilized to remove the containers from the detection stations. Preferably, an operator at each station monitors the operation thereof and is notified, preferably via an audible signal and a computer monitor, when contraband is detected at that station. Alternatively, a single operator can monitor a plurality of such contraband detection stations.

The target is formed so as to be generally disk shaped and preferably has a cavity formed therethrough within which water flows, so as to provide cooling therefor. According to the preferred embodiment of the present invention, the disk comprises two generally planar beryllium walls defining the cavity through which cooling water flows. The disk preferably comprises coatings of $^{13}C$ and $^{34}S$ so as to facilitate the detection of $^{14}N$ and $^{35}Cl$ via gamma ray absorption.

These, as well as other advantages of the present invention will become more apparent from the following description and drawings. It is understood that changes in the specific structure shown and described may be made within the scope of the claims without departing from the spirit of the invention.

BRIEF DESCRIPTION OF THE DRAWINGS

FIG. 4 is a functional block diagram of the multiple station contraband detection system of the present invention;

DETAILED DESCRIPTION OF THE PREFERRED EMBODIMENT

Figure 1:
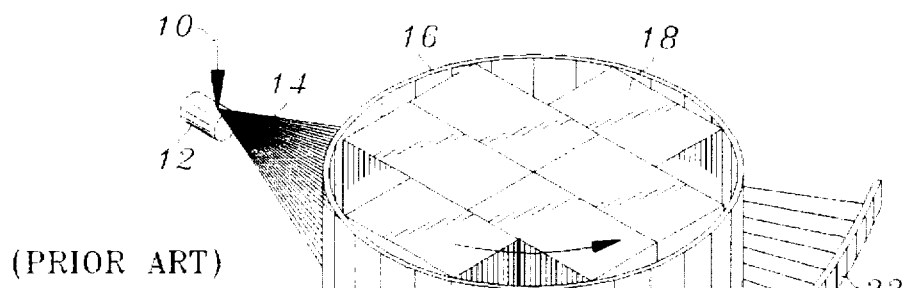
FIG. 1 is a schematic representation of a contemporary gamma ray absorption contraband detection station wherein a proton beam is utilized to excite gamma radiation from a target configured as a drum, thereby producing a gamma ray beam of approximately 53 degrees dispersion, which is suitable for use in only a single contraband detection station.

The detailed description set forth below in connection with the appended drawings is intended as a description of the presently preferred embodiment of the invention, and is not intended to represent the only form in which the present invention may be constructed or utilized. The description sets forth the functions and sequence of steps for constructing and operating the invention in connection with the illustrated embodiment. It is to be understood, however, that the same or equivalent functions may be accomplished by different embodiments that are also intended to be encompassed within the spirit and scope of the invention. The multiple station contraband detection system of the present invention is illustrated in FIGS. 2 through 11 which depict a presently preferred embodiment of the invention. FIG. 1 depicts the use of a contemporary cylindrically configured target in a single station contraband detection system.

Referring now to FIG. 1, according to contemporary methodology, a proton beam 10 is incident upon a target 12 which is configured generally as a cylinder. The cylinder is typically comprised of copper or copper alloy having coatings of $^{13}C$ and $^{34}S$, so as to produce gamma rays which are absorbed by nitrogen and chlorine. The cylinder is rotated so as to provide thermal dissipation and thereby prevent heat buildup at any particular location thereon. The proton beam 10 excites a 360 degrees fan of gamma radiation 14 having a useful dispersion angle or field of view of approximately 53 degrees. In the prior art, the rotating target axis is tilted so that 53 degrees of gamma rays are reflected by the target. The gamma ray fan is only usable over about 53 degrees due to scattering and attenuation covered by the target structure. As those skilled in the art will appreciate, a field of view of 53 degrees is only sufficient to provide for the scanning of a single container or drum 16 having a plurality of separate test articles or bags 18 contained therein. The drum 16 is rotated within the field of view of the gamma radiation 14 about the axis 20 thereof and is also translated up and down along the axis 20 thereof, so as to insure the complete and reliable detection of contraband contained within the baggage 18. An array of gamma ray detectors 22 measures the intensity of the gamma rays after they have passed through the rotation and translation drum 16.

Thus, as the drum 16 is rotated and translated, contraband such as illegal drugs and explosives pass through the path of the gamma rays 14. The gamma rays 14 are selectively absorbed by compounds containing elements such as chlorine and nitrogen, such that the gamma rays 14 are attenuated prior to being sensed by gamma ray detectors 22.

Thus, an operator is notified as to the possibility of baggage 18 within the drum 16 containing contraband. The baggage 18 may then be manually inspected in order to verify the presence of contraband.

However, one problem associated with such contemporary contraband detection methodology is the cost per article inspected. Since a large proportion of the costs associated with the operation of such a gamma ray absorption contraband detection system are associated with the construction and maintenance of the linear accelerator and target, it would substantially reduce the cost per article tested if the number of detection stations for a particular linear accelerator could be substantially increased. However, due to the contemporary use of a target configured as a cylinder, the angle of dispersion of gamma rays from the target is strictly limited, such that each linear accelerator can support only a single detection station.

Figure 2:
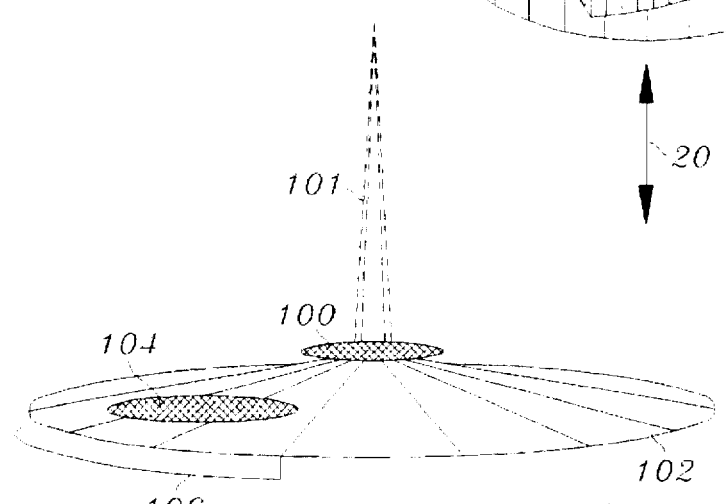
FIG. 2 is a schematic representation of a proton beam incident upon a gamma ray target configured as a disk according to the present invention, so as to provide a 360 degree gamma ray resonant cone suitable for servicing a plurality of separate detection stations.

Referring now to FIG. 2, according to the present invention a target 100 is configured so as to be generally disk shaped. It produces a resonant cone 102 of 360 degrees when struck by proton beam 101. The resonant cone 102 of 360 degrees may be easily divided into four portions, each portion having a field of view of approximately 53 degrees, so as to facilitate detection at four separate stations 104 simultaneously.

Figure 3:
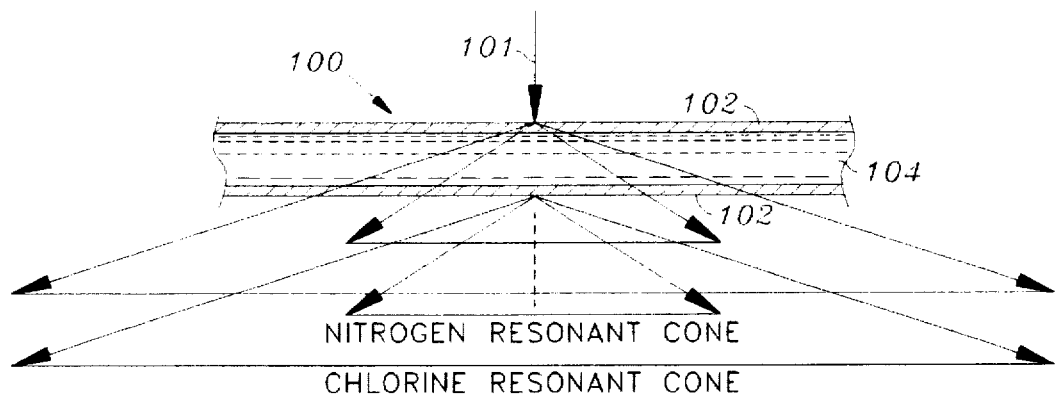
FIG. 3 shows the angles of the nitrogen resonant cone and the chlorine resonant cone for a proton beam incident upon the disk-shaped target of the present invention.
Figure 1:
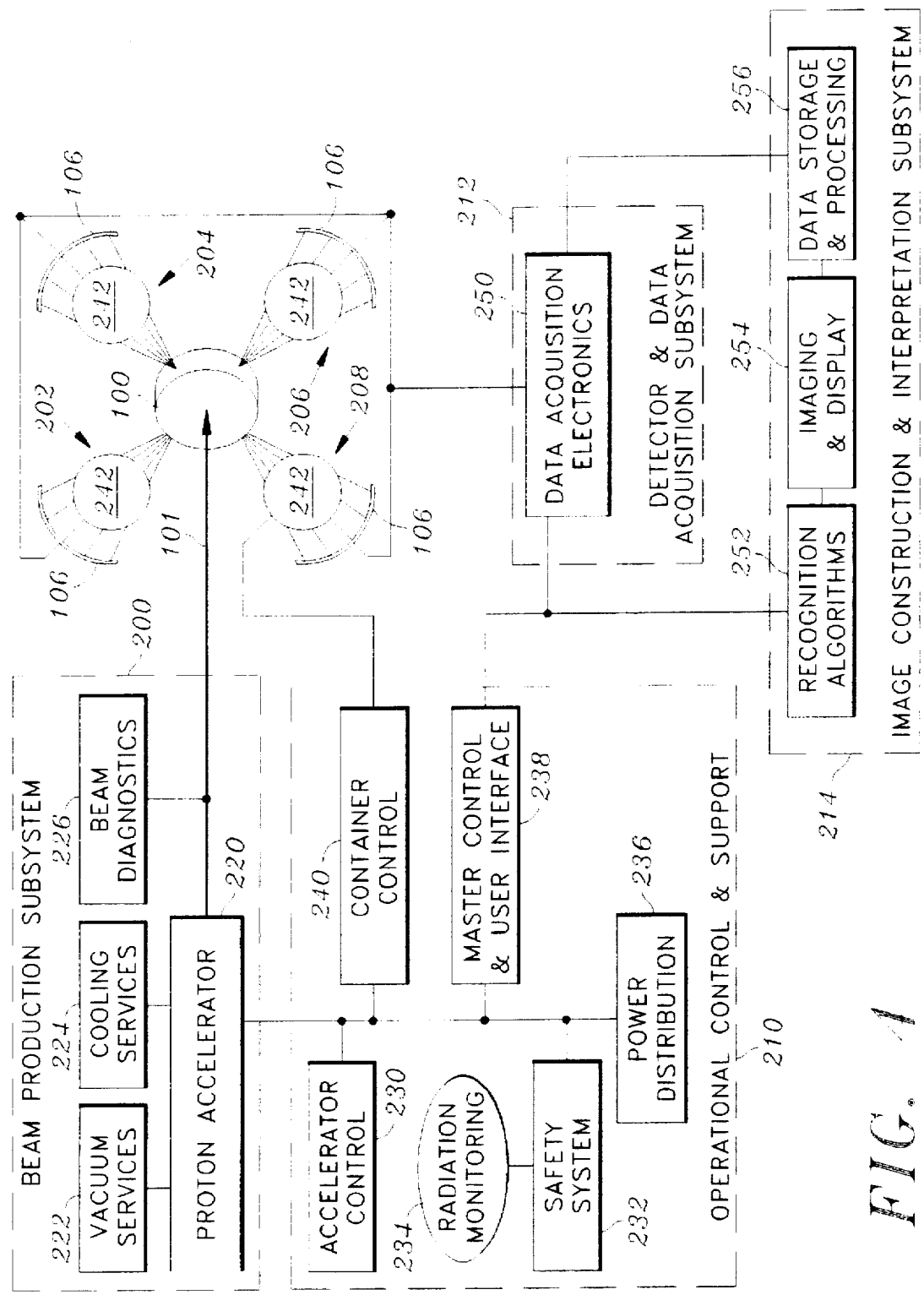

Referring now to FIG. 3, the angle with respect to the normal 103 (which defines the sharpness of the resonant cone) at which the 360 degrees resonant cone is formed is dependent upon which target coating, i.e., $^{13}C$ or $^{34}S$, is excited. This in turn is dependent upon the energy of the proton beam, as discussed below. Thus, the proton beam 101 striking the disk-shaped target 100 produces either a resonant cone having an angle of 80.66 degrees for the detection of nitrogen or a resonant cone having an angle of 82 degrees for the detection of chlorine.

The linear accelerator (220 of FIGS. 4 and 5) is configured so as to provide a DC current $\geq 10$ mA and so as to provide a stream of protons at either 1.75 MeV or 1.89 MeV±12 KeV. Proton beam emittance is preferably 0.12 $\pi$millimeter milliradians (rms). The use of a 1.75 MeV proton beam excites an 80.7 degree resonant gamma ray cone from the $^3C$ coating of the target for the detection of nitrogen, while the use of a 1.89 MeV proton beam excites an 82 degree resonant gamma ray cone from the $^{34}S$ coating of the target for the detection of chlorine. Thus depending upon which proton beam energy is selected (and consequently which target coating is excited), the resultant resonant gamma rays are preferentially absorbed by either nitrogen or chlorine, thereby facilitating their detection.

Since the angles at which the gamma rays are produced by the target are so close (80.7 degrees for nitrogen and 80.66 degrees for chlorine), a common array of segmented gamma ray detectors may be utilized to detect gamma rays passing through the drum 16, as discussed in detail below.

According to the preferred embodiment of the present invention, the target 100 comprises two spaced apart, generally parallel walls 102 formed of beryllium having a single front surface coated with $^{13}C$ and $^{34}S$. A cavity 104 is formed intermediate the two walls 102 to accommodate water flow therein for cooling the target 100. The target is preferably 1 to 3 feet in diameter and ⅛ to ½ inch in thickness.

Referring now to FIG. 4, the present invention generally comprises a beam production subsystem 200 for providing gamma rays to each of the contraband detection stations 202, 204, 206, and 208. An operational control and support system 210 facilitates operation of the multiple station contraband detection system as described in detail below. The detector and data acquisition subsystem 212 collects data from the detector arrays 106 and provides the same to image construction and interpretation subsystem 214 for processing.

The beam production system 200 comprises the proton accelerator 220 and the target 100. The proton accelerator provides a beam of protons 101 having energies of either 1.75 MeV or 1.89 MeV, so as to facilitate the detection of either nitrogen or chlorine, respectively. Vacuum services 222 provide the vacuum necessary for the generation of the proton beam 101 and communication of proton beam 101 to the target 100. Cooling services 224 provide the required cooling for the proton accelerator 220. Beam diagnostics 226 monitor the proton beam 101 so as to assure proper operation of the proton accelerator and auxiliary equipment.

The operational control and support section 210 comprises accelerator control 230 for providing control of the proton accelerator 220. A safety system 232 having a radiation monitoring subsystem 234 monitors safety related items. Power distribution 236 provides power to the proton accelerator 220 and support equipment. Master control and user interface 238 provides the primary means for the operator to control the multiple station contraband detection system of the present invention. Container control 240 controls movement of the drums 273 (FIG. 8) on the conveyors 301 and 303, and the rotation and translation tables 272, as discussed in detail below. Container handling 242 facilitates movement of the containers from the incoming conveyor belts 301 to the rotation and translation tables 272 and from the rotation and translation tables 272 to the outgoing conveyor belts 303.

Detector arrays 106 preferably comprise bismuth germanium oxide (BGO)gamma ray detectors for sensing the intensity of the gamma rays after they have passed through the baggage contained within the drums 273. According to the preferred embodiment of the present invention, two adjacent horizontal rows of such detectors define the array 106. This has been found to provide sufficient resolution so as to reliably indicate which bag contained in a drum 273 most likely contains sensed contraband.

The detection and data acquisition subsystem 212 comprises data acquisition electronics 250 for receiving the outputs of the detector arrays 106 and for conditioning the same.

Image construction and interpretation subsystem 214 utilizes recognition algorithms 252 for determining the likelihood that a sensed detector signal indicates the presence of contraband. The recognition algorithms 252 provide an output indicative of the sensed signals to imaging and display system 254 so as to alert an operator of the likely presence of contraband. Data storage and processing 256 provides for the storage of data indicative of likely contraband being contained within a particular piece of baggage, for future evidentiary purposes.

Figure 5:
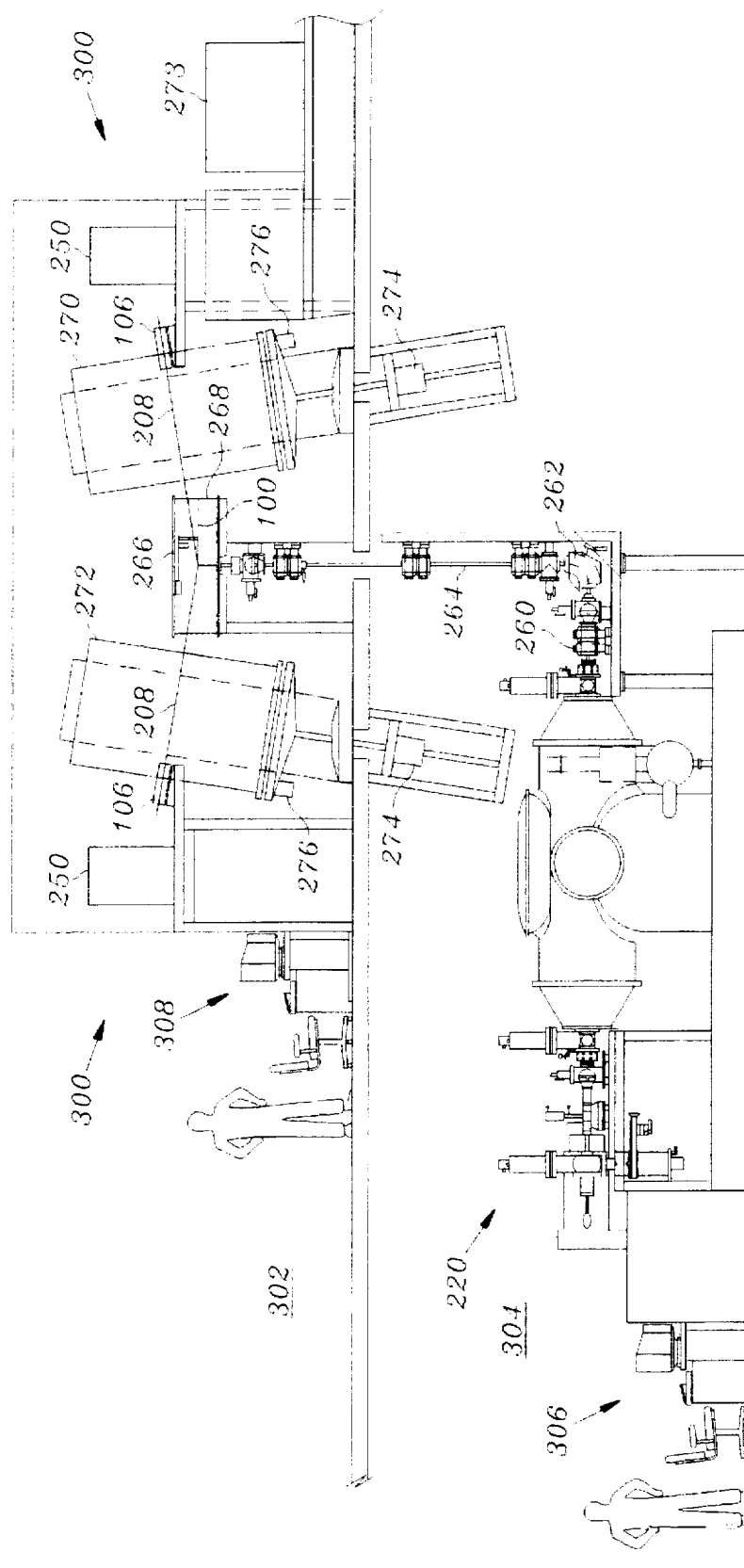
FIG. 5 is a side view, partially in section, of the multiple station contraband detection system of the present invention.

Referring now to FIG. 5, a plurality of individual contraband detection stations 300 are preferably disposed upon one floor 302 of a building while the proton accelerator 220 is located upon the floor below 304. A work station 306 allows an operator to control and monitor the proton accelerator 220 on the lower floor and a work station 308 allows an operator to control and monitor the contraband detection system 300 on the upper floor 302. Optionally, a plurality of operators may be accommodated for the proton accelerator and/or the contraband detection stations. For example, four work stations 308 may be provided, one for each contraband inspection station.

Figure 6:
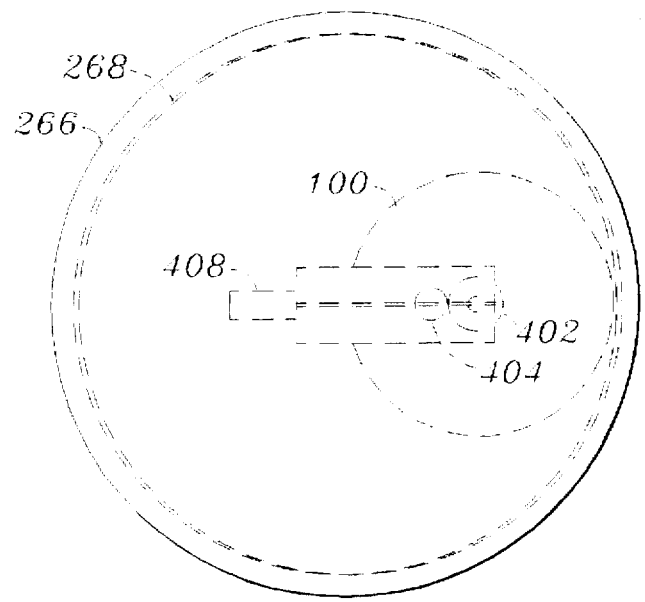
FIG. 6 is a plan view of the target vacuum vessel showing in dashed lines the target of FIG. 5 contained therein.
Figure 7:
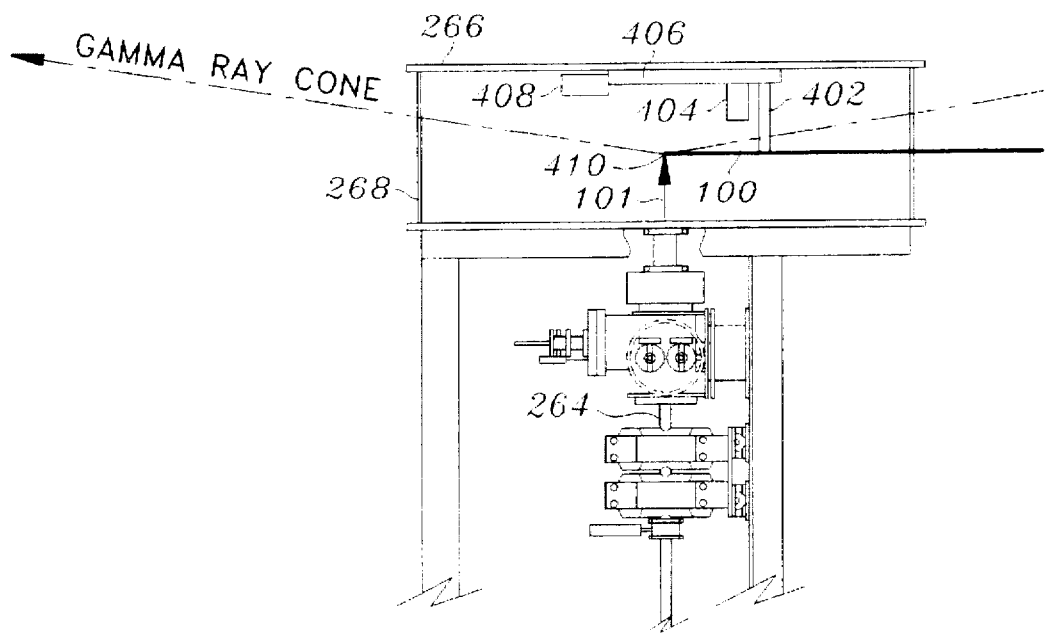
FIG. 7 is a side view, partially in cross section, of the vacuum vessel and target of FIG. 6.

Protons provided by accelerator 220 travel through proton conduit 260, bend 262, and proton conduit 264, and are then directed upon target 100 (better shown in FIGS. 6 and 7). The target 100 is disposed within vacuum vessel 266 comprised of gamma ray transparent beryllium walls 268.

Drums 273 disposed upon rotation and translation tables 272 are rotated about their axis and also move up and down in order to assure that they are adequately scanned by gamma rays 208 produced by the impact of the proton beam 101 upon the target 100.

A ball screw linear drive 274 moves each rotation and translation table 272 up and down while a rotation motor 276 effects rotation of each rotation and translation table. Gamma ray detectors 106 sense the intensity of the gamma rays 208 after they have passed through the drum 272. As discussed in detail below, contraband contained within baggage contained in the drums 273 selectively absorbs gamma rays so as to vary the sensed intensity thereof and thereby provide an indication as to the presence of such contraband. The outputs of the gamma ray detectors 106 are provided to data acquisition electronics 250 (FIG. 4) and the output of the data acquisition electronics 250 is provided to the recognition algorithms 252 and the data storage and processing system 256.

Referring now to FIGS. 6 and 7, the target 100 is generally configured as a disk which is rotatable about its center via shaft 402, which is rotatable via rotation motor 404. Rotation motor 404 and shaft 402 are preferably mounted upon translation platform 406 which is movable via translation motor 408. Thus, the target 100 can be rotated and translated so as to vary the impact point 410 at which the proton beam 101 strikes the target 100. In this manner, localized heat buildup is minimized since the proton beam is not allowed to impact upon any particular portion of the target 100 for a prolonged period of time.

The target is disposed within vacuum vessel 266, having beryllium side wall 268. The beryllium side wall 268 is transparent to the gamma radiation generated when the proton beam 101 strikes the target 100. Thus, the gamma radiation is free to pass through the test articles to be incident upon gamma ray detectors 106.

Figure 8:
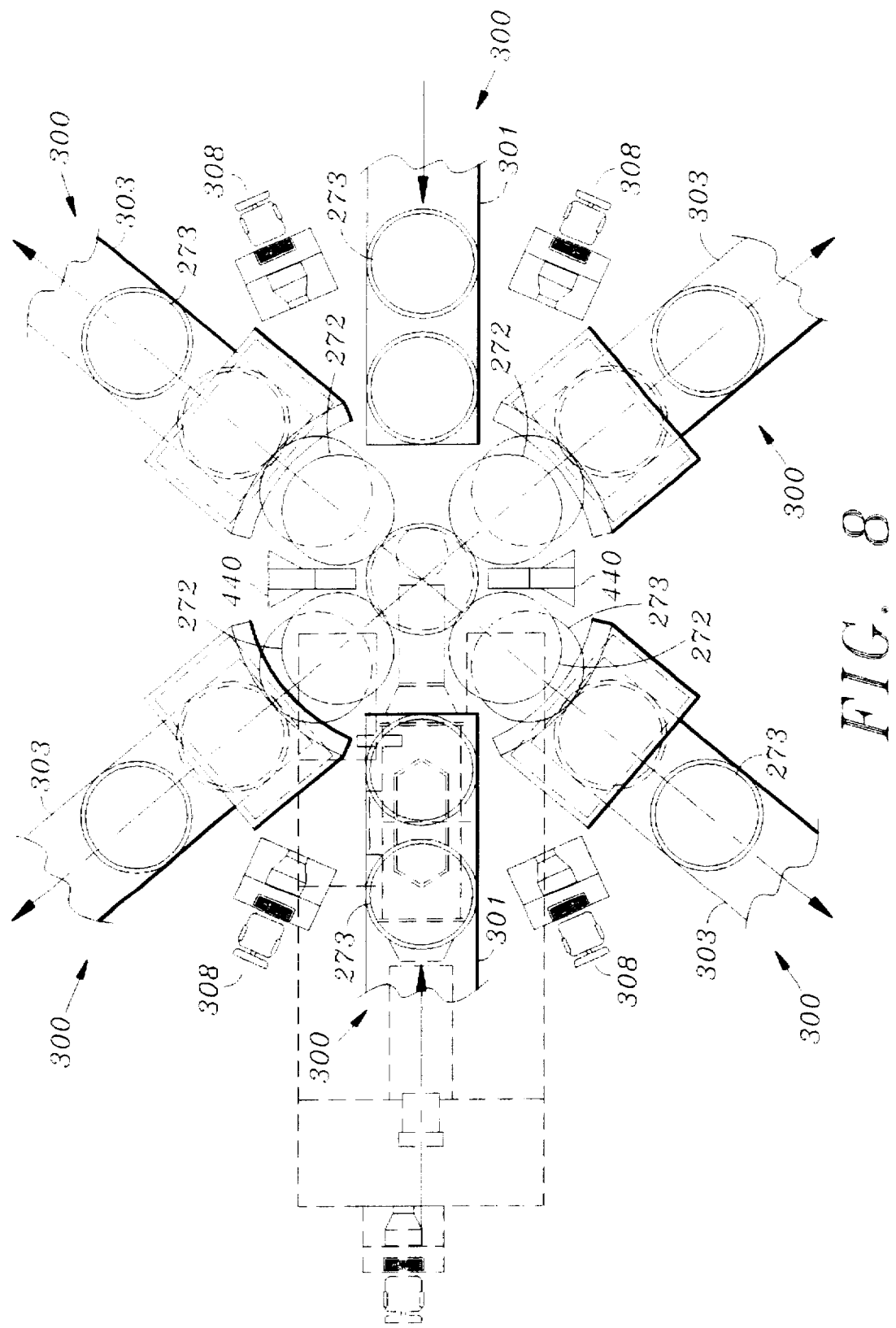
FIG. 8 is a plan view of the four detection stations of the present invention showing the input and output conveyors for moving drums containing test items and showing the rotation and translation tables used to scan the test items.

Referring now to FIG. 8, the conveyor and container handling system for transporting drums 273 to the rotation and translation tables 272 for, positioning the drums 273 upon the rotation and translation tables 272, for removing the drums 273 from the rotation and translation tables 272, and for transporting the drums 273 away from the rotating and translation tables 272, is illustrated.

According to the preferred embodiment of the present invention, the multiple station gamma ray absorption contraband detection system comprises four individual detection stations 300. Two input conveyor 301 are configured such that each input conveyor 301 services two adjacent detection stations 300. Each detection station 300 has a dedicated output conveyor 303.

The drums 273 are transported by the input conveyors 301 to a position proximate to rotation and translation tables 272. Drum handling equipment, not shown, then transfers each drum from the input conveyor 301 to a selected one of the two adjacent rotation and translation tables 272. Preferably, the handling equipment alternates between the two rotation and translation tables 272 such that one drum is placed upon that rotation and translation table 272 to the drum's 273 left, then the next drum is placed upon the rotation and translation table 272 to the drum's 273 right, and the process repeats indefinitely.

Once a drum 273 is positioned upon a rotation and translation table 272, the table 272 then begins to rotate and translate in a manner which facilitates accurate and reliable scanning of the items contained within the drum 273. Once scanning process is complete, handling equipment (not shown) then moves the drum 273 from the rotation and translation table 272 to a dedicated output conveyor 303 which then moves the drum 273 away from the contraband detection station. Guides 440 stabilize and restrain the drums 273 as they are loaded onto the rotation and translation tables 272 and removed therefrom.

The contraband detection process is preferably monitored at a dedicated work station 308 by a dedicated operator.

Figure 9:
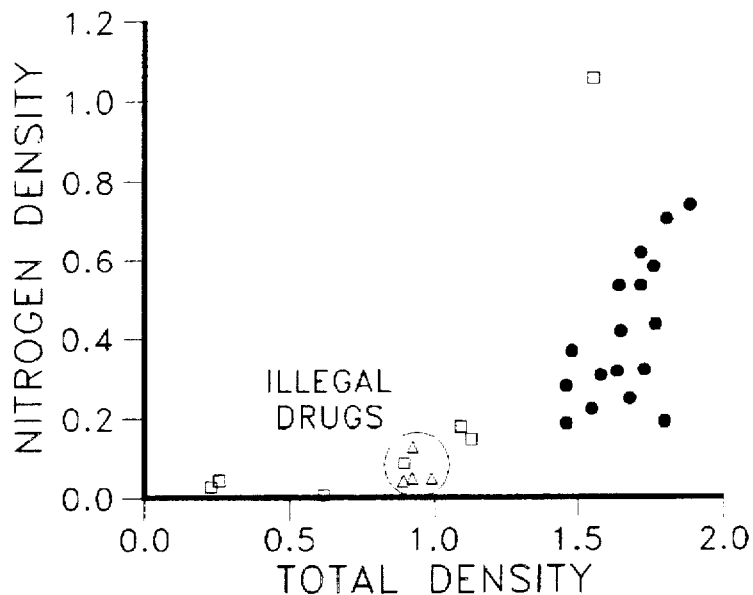
FIG. 9 is a plot of nitrogen density versus total density showing the separation of illegal drugs, explosives, and other materials.
Figure 10:
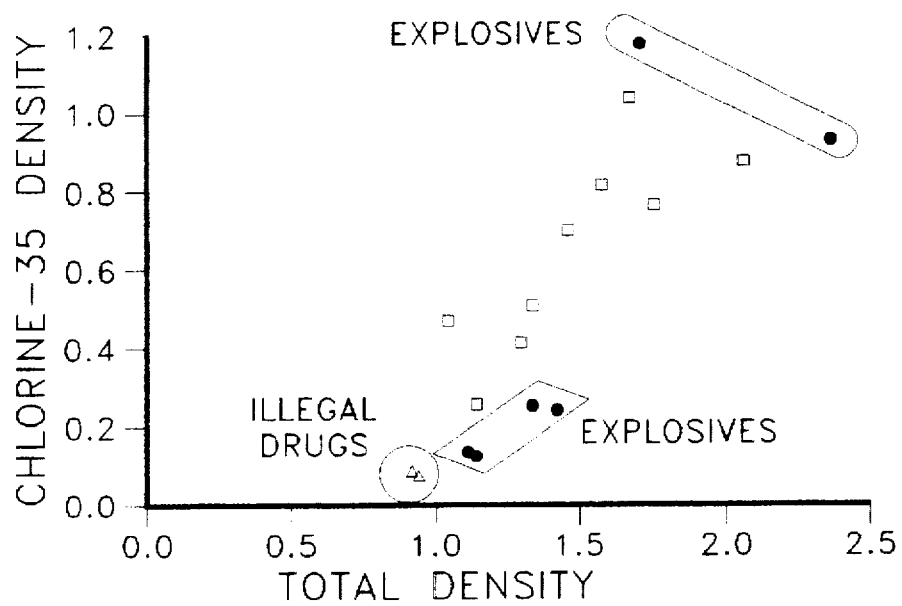
FIG. 10 is a plot of chlorine density versus total density showing the separation of illegal drugs, explosives, and other materials.

Referring now to FIGS. 9 and 10, testing has shown that illegal drugs, as indicated by the small solid triangles, and explosives, as indicated by the small circles, tend to be positioned apart from common material, as indicated by small squares, when plotted on a nitrogen density versus total density graph. Similarly, drugs and explosives tend to be located at different positions from other materials on a chlorine density versus total density plot. These differences in the responses of common materials, explosives, and drugs to gamma rays facilitates the reliable detection of such contraband materials. The recognition algorithms 252 check to see if the response of a test article is located at the position on the nitrogen density versus total density and chlorine density versus total density plots which is indicative of such contraband. Then if contraband is indicated, the baggage is manually inspected.

Figure 11:
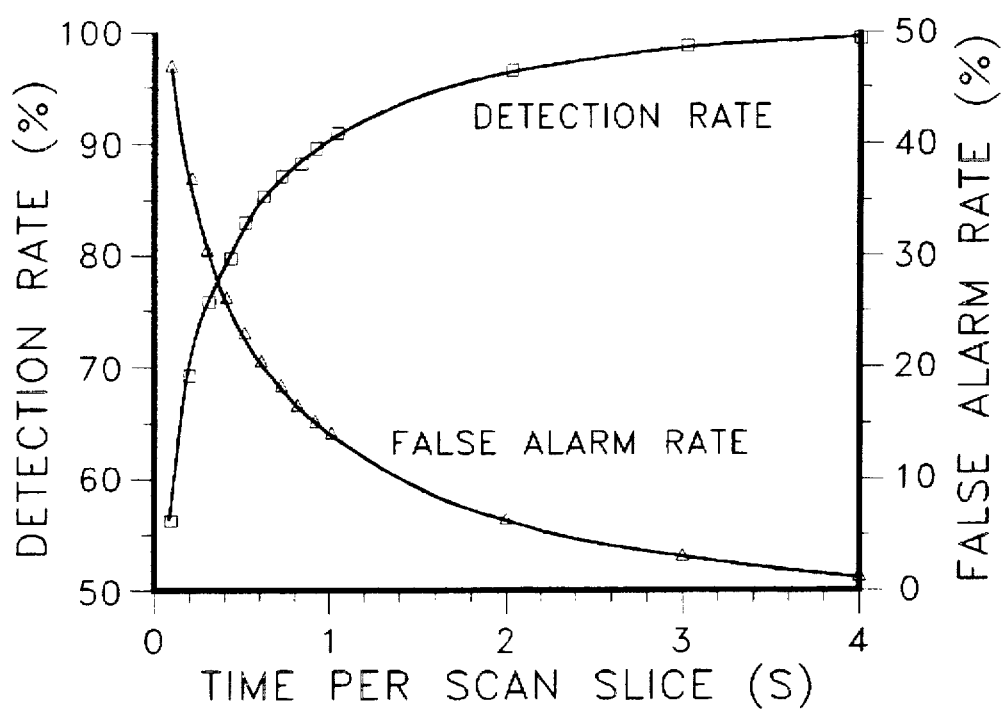
FIG. 11 is a typical plot of detection rate and false alarm rate versus time per scan slice showing that the rate at which contraband is detected increases as the time per slice increases, and also showing that the false alarm rate decreases as time per slice increases.

Referring now to FIG. 11, as the time per scan slice increases, the detection rate increases, thereby providing more reliable and effective detection of contraband. As would be expected, the false alarm rate decreases with increased time per scan.

It is understood that the exemplary multiple station gamma ray absorption contraband detection system described herein and shown in the drawings represents only a presently preferred embodiment of the invention. Indeed, various modifications and additions may be made to such embodiment without departing from the spirit and scope of the invention. For example, various different physical configurations of the conveyor and handling system are contemplated. Additionally, those skilled in the art will appreciate that fewer or more than four detection stations may be accommodated by the 360 degrees resonant gamma ray cone of the present invention. Thus, these and other modifications may be obvious to those skilled in the art and may be implemented to adapt to the present invention for use in a variety of different applications.

What is claimed is:

1. A target for a gamma ray absorption contraband detection system, said target comprising:
   a) a disk formed of beryllium having a gamma ray producing material formed thereon; and
   b) wherein said disk provides a 360 degrees resonant gamma ray cone when a proton beam is incident thereon so as to facilitate operation of plural detection stations simultaneously therewith.

2. The target as recited in claim 1 wherein said disk comprises a cavity formed therein through which water is flowable so as to provide cooling therefore.

3. The target as recited in claim 1 wherein said disk comprises two generally planar, generally parallel beryllium walls defining a cavity within which water provides cooling for the target.

4. The target as recited in claim 1 further comprising a motor drive for effecting translation of said disk so as to vary the radial position at which the proton beam strikes the disk.

5. The target as recited in claim 1 further comprising a motor drive for effecting translation of said disk so as to vary the radial position at which the proton beam strikes the disk.

6. A multiple station gamma ray absorption contraband detection system, said system comprising:
   a) a proton source;
   b) a target upon which protons from said proton source are incident, said target comprising:
      (i) a disk formed of beryllium having a gamma ray producing material formed thereon;
      (ii) wherein said disk provides a 360 degree resonant gamma ray cone; and
   c) at least two detection stations using a portion of the 360 degree resonant gamma ray cone to facilitate detection of contraband.

7. The multiple station gamma ray absorption contraband detection system as recited in claim 6 wherein four detection stations each use between approximately 45 degrees and approximately 90 degrees of the 360 degrees resonant gamma ray cone.

8. The multiple station gamma ray absorption contraband detection system as recited in claim 6 wherein four detection stations each use approximately 53 degrees of the 360 degrees resonant gamma ray cone.

9. The multiple station gamma ray absorption contraband detection system as recited in claim 6 wherein each detection station comprises:
   a) a conveyor for transporting a test article into that portion of the gamma ray cone used by the station; and
   b) at least one detector configured to sense gamma rays which have passed through the test article.

10. The multiple station gamma ray absorption contraband detection system as recited in claim 9 further comprising a table which translates and rotates the test article within the proton beam.

11. The multiple station gamma ray absorption contraband detection system as recited in claim 9 further comprising a plurality of containers into which test articles are disposed, said containers being moved via said conveyor into the gamma ray cone.

12. The multiple station gamma ray absorption contraband detection system as recited in claim 9 wherein said detector(s) comprise a plurality of detectors defining an array thereof.

13. The multiple station gamma ray absorption contraband detection system as recited in claim 9 wherein said detector(s) comprise two rows of detectors generally defining an arc.

14. The multiple station gamma ray absorption contraband detection system as recited in claim 9 wherein said detector(s) comprise bismuth germanium oxide detectors.

15. The multiple station gamma ray absorption contraband detection system as recited in claim 9 wherein said conveyor comprises:
   a) at least one table for rotation and translation a container containing at least one test article;
   b) at least one incoming conveyor belt for bringing the container near said table(s);
   c) a first handler for each incoming conveyor belt for moving the container from the incoming conveyor belt to a table;
   d) at least one outgoing conveyor belt; and
   e) a second handler for each outgoing conveyor belt for moving the container from the table to the outgoing conveyor belt.

* * * * *